(12) United States Patent
Jones et al.

(10) Patent No.: US 7,363,206 B2
(45) Date of Patent: Apr. 22, 2008

(54) COMPOSITIONAL MODELING AND PYROLYSIS DATA ANALYSIS METHODS

(75) Inventors: Peter J. Jones, Dhahran (SA); Henry L. Halpern, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 177 days.

(21) Appl. No.: 10/555,805

(22) PCT Filed: May 7, 2004

(86) PCT No.: PCT/US2004/014443

§ 371 (c)(1),
(2), (4) Date: Jun. 22, 2006

(87) PCT Pub. No.: WO2004/102156

PCT Pub. Date: Nov. 25, 2004

(65) Prior Publication Data

US 2007/0162264 A1    Jul. 12, 2007

(51) Int. Cl.
    *G01N 33/24* (2006.01)
(52) U.S. Cl. .............. 703/10; 703/2; 702/6; 702/13
(58) Field of Classification Search ............... 703/2, 703/10; 702/6, 9, 11, 12, 13; 73/152.11
    See application file for complete search history.

(56) References Cited

U.S. PATENT DOCUMENTS 5,866,814 A * 2/1999 Jones et al. ............ 73/152.11
6,823,298 B1 * 11/2004 Jones et al. ................ 703/10

* cited by examiner

*Primary Examiner*—Donald E McElheny, Jr.
(74) *Attorney, Agent, or Firm*—Abelman, Frayne & Schwab

(57) ABSTRACT

Methods for processing pyrolytic characterizing data (pcd) from reservoir rock samples obtained from known geographical locations under circumstances that are encountered during the drilling of wells provide information that is important for assessing the relative amounts of various hydrocarbon and organic matter types found in the reservoir and for characterizing the reservoir quality and preparing compositional modeling data, and include the steps of comparing the pcd for known end-member components typically found in the geographical location with the pcd derived from test samples and applying mathematical analyses to identify the predicted composition and quantitative measure of end-members. The method is applied to model hydrocarbon moveability, reservoir injectivity; contaminants and soil an aquifer pollutants.

28 Claims, 12 Drawing Sheets

TABLE 1

| TITLE | Sample Report | | | | | | |
|---|---|---|---|---|---|---|---|
| PROJECT | sample | | | | | | |
| INSTRUME | POPI-1 | | | | | | |
| OPERATOR | | | | | | | |
| | | | | | | | |
| WELL NAME | | | | | | | |
| FILE NAME | C:\Program Files\POPI\Data\UTMN1229\U1229_06.raw | | | | | | |
| DEPTH | | | | | | | |
| DATE | November 16 2002 | | | | | | |
| TIME | ######## | | | | | | |
| | | | | | | | |
| SEQUENC | C:\Program Files\POPI\Data\UTMN1229.pas | | | | | | |
| ANALYSIS | C:\Program Files\POPI\195630.PAR | | | | | | |
| | | | | | | | |
| PROGRAM | NUM | ITEMP | ITIME | RATE | FTEMP | FTIME | |
| PROGRAM | 1 | 195 | 3 | 25 | 630 | 0 | |
| | | | | | | | |
| RESULT | SAMPLEN | SAMPLET | AMOUNT | LV | TD+TC | TMAX | TMIN | TD |
| RESULT | sample | SMP | 38.9 | 5.39362 | 12.95638 | 260.8579 | 400.1474 | 9.303264 |
| TC | TD/TC | LV+TD+TC | POPI | LV/TC+TD | API[S1/S2] | API[S1/S1+S2]@TMIN | |
| 3.653116 | 2.546665 | 18.35 | 7.409852 | 0.416291 | 11.36505 | 30.73751 | |
| DATA | SIGNAL | OVEN(°C) | TD+TC | Sum | Diff | | |
| 0 | 574464 | 66.8 | | | | | |
| 1 | 1264110 | 83 | | | | | |
| 2 | 2772130 | 98.8 | | | | | |
| 3 | 5664670 | 112.6 | | | | | |
| 4 | 10013790 | 124.6 | | | | | |
| 5 | 16174618 | 134.7 | | | | | |
| 6 | 24601475 | 143.4 | | | | | |
| 7 | 30782832 | 151 | | | | | |
| 8 | 37969810 | 157.4 | | | | | |
| 9 | 46847259 | 163.1 | | | | | |
| 10 | 54391029 | 167.8 | | | | | |
| DATA POINTS 11 TO 599 DELETED FOR BREVITY | | | | | | | |
| 600 | 564035 | 610.8 | 405002.5 | 4.26E+09 | 405002.5 | | |
| 601 | 561627 | 611.7 | 403273.5 | 4.26E+09 | 403273.5 | | |
| 602 | 558608 | 612.6 | 401105.7 | 4.26E+09 | 401105.7 | | |
| 603 | 556394 | 613.3 | 399515.9 | 4.26E+09 | 399515.9 | | |
| 604 | 554090 | 614.1 | 397861.6 | 4.26E+09 | 397861.6 | | |
| 605 | 551880 | 615 | 396274.7 | 4.26E+09 | 396274.7 | | |
| 606 | 549402 | 615.7 | 394495.4 | 4.26E+09 | 394495.4 | | |
| 607 | 547742 | 616.6 | 393303.4 | 4.26E+09 | 393303.4 | | |
| 608 | 544603 | 617.4 | 391049.5 | 4.26E+09 | 391049.5 | | |
| 609 | 542205 | 618.2 | 389327.6 | 4.26E+09 | 389327.6 | | |
| 610 | 538718 | 619 | 386823.8 | 4.26E+09 | 386823.8 | | |
| 611 | 536627 | 619.8 | 385322.3 | 4.26E+09 | 385322.3 | | |

FIG. 11

COMPOSITIONAL MODELING AND PYROLYSIS DATA ANALYSIS METHODS

FIELD OF THE INVENTION

This invention relates to the interpretation, analysis, modification and use of data generated by the pyrolysis of samples of reservoir rock obtained from known locations in oil fields for the modeling and characterization of the reservoir.

BACKGROUND OF THE INVENTION

One analytical method used to detect the presence of hydrocarbons in reservoir rock samples is known as open-system pyrolysis. In open-system pyrolysis, a temperature-programmed instrument heats a small amount of a ground rock sample, usually less than 100 mg. The sample is held for three minutes at a starting temperature of 180° C. and then heated to 600° C. at a rate of 25° C. per minute. During this programmed heating, the hydrocarbons driven from the rock sample are recorded as a function of temperature. The pyrolysis equipment is well-known in the art and is available from commercial sources. In the attached drawings, FIG. 1 shows a typical prior art instrument output plot that is known as a pyrogram. A typical analysis results in three peaks. The first is composed of hydrocarbons that can be volatilized, desorbed, and detected while the temperature is held constant for the first 3 minutes of the procedure at or below about 180° C. These are referred to as light volatile hydrocarbons, or light volatiles (LVHC, or LV).

The next phase of pyrolysis consists of a programmed temperature increase from 180° C. to 600° C. that results in two additional distinct peaks. The first of these peaks occurs between 180° C. and about 400° C., and corresponds to thermal desorption of solvent-extractable bitumen, or the light oil fraction. These are called thermally distilled hydrocarbons (TDHC, or TD). The second additional peak (third peak overall) occurs after about 400° C., generally after a minimum in pyrolytic yield is observed. The temperature corresponding to the minimum in pyrolytic yield is referred to as $T_{min}$ and extends typically to about 550° C. This peak is due to the pyrolysis (cracking) of heavier hydrocarbons, or asphaltenes. The materials that thermally crack are called thermally cracked hydrocarbons or "pyrolyzables" (TCHC, or TC).

A specialized analytical procedure that is utilized to characterize reservoir rock is know as the Pyrolytic Oil-Productivity Index, or POPI, and is disclosed in U.S. Pat. No. 5,866,814, the disclosure of which is incorporated herein by reference. The POPI and its associated methods as developed in the prior art are most useful when applied to the characterization of oil productive reservoirs. The analysis of core samples is principally concerned with the characterization of hydrocarbon columns to assess oil-water transition zones, free water levels, and the occurrence of tar mats.

The prior art's approach to the use of pyrolysis data has been directed to the assessment of bulk parameters and has not considered the discreet manner in which the data can be exploited to provide more refined characterizing information as has been accomplished herein with the Compositional Modeling method.

The nature of the laboratory analysis of core samples is significantly different than the type of work that is conducted in the field at drilling sites where pyrolysis data is to be used for the assessment of reservoir quality or reservoir injectivity, and tar occurrence, in order to optimize the placement of horizontal power injection wells and hydrocarbon production wells. The known methodology has been found to have limited utility in characterizing reservoir quality in oil-water transition zones.

The application of the prior art POPI methods in the field were not originally expected to be directed to tar detection or, even to a lesser extent, to determining the apparent water saturation ($AS_w$) and other reservoir parameters. Difficulties in the application of the POPI method became apparent during the field work, when significant contamination from drilling additives was observed in the POPI results, as well as a reduction in hydrocarbon yield from cutting samples collected from oil transition zones when these were compared to the pyrograms and POPI results based on core chip samples tested in the laboratory.

The compositional modeling method (the subject invention) overcomes these difficulties through the modeling of the pyrolytic response in terms of end-member components that are present in a reservoir system. It was further adapted to include the step of removing this contamination signal in order to reveal the unaltered characteristics of staining on the cuttings samples. This processing step required the treatment of contamination by two end-members, as contamination from drilling mud could not be modeled as a single component. In order to obtain an adequate match at well drilling sites, the contributions to the pyrolytic signal from diesel contamination and from other mud additives had to be modeled as separate components. Accounting for these additional end-member components made possible the assessment of the unaltered composition of staining on drill cutting samples.

The development of these novel means to quantify the component of the hydrocarbon signal that is attributable to contamination sources led to another novel method for producing useful characterizing information. By providing a plot of the various pyrolysis components alongside well log data it was discovered that the amount of residual contamination that remains after samples of the drill cuttings have been washed is an indication that reservoir fluids have been displaced by the drilling mud that is circulated in the well bore during the drilling operation. Thus, it has been found that in reservoirs where drilling mud cannot invade the pore space, the amount of contamination is either much lower or not present. This observation leads to the conclusion that the residual drilling mud is easily washed from outside surfaces, because it cannot enter the matrix of lower quality rock in the reservoir.

Thus, the method of the invention provides data and means for the assessment of moveable fluids, which is one of the most important parameters in reservoir characterization. In determining this characteristic by pyrolysis, the incursion is detected by quantifying the remnant component in the sample. The theory supporting the methodology is analogous to the principle used in assessing moved hydrocarbons from well logs, where the invasion of mud filtrate into the reservoir rock is detected by differences in the electrical resistivity profile that is observed. The method of analysis of the invention differs from the well log method in the same way that POPI differs in assessing reservoir productivity, i.e., it is based on a direct measurement from a rock sample and therefore provides an independent assessment of fluid moveability.

The method of the invention is equally applicable to the assessment of fluid moveability in the oil-water transition zone as it is in the oil column. This attribute is particularly important for the optimization of the placement of horizontal power water injector wells. The method can provide an assessment of whether tar is present and, if so, in what quantity. It can also be an indicator of whether reservoir fluids can be moved and provide a better understanding of what amount of tar saturation will adversely affect injectivity.

In order to facilitate a full and comprehensive understanding of the novel methods of the invention there follows a listing of definitions of terms that will be used in the detailed description of the invention.

It is therefore a principal present invention to provide improved information and data based on the POPI method as applied to rock samples gathered in filed drilling operations.

The following are related and specific objects of the invention:

a. to provide a method for modeling the composition of organic matter present in rock samples through an iterative process of reconstructing pyrolysis curves from end-member components that are known to exist in an oil reservoir;

b. to provide a method for correcting data for samples that appear to be composed of one principal end-member component by factoring out or subtracting a variable percentage of the interfering end-member component;

c. to provide a method for assessing pyrolytic characteristics of contaminants or other organic components that occur in relatively low concentrations in samples, but nonetheless are components that require identification and quantifying in order to obtain accurate modeling results;

d. to provide a method for adjusting pyrolytic parameters by subtracting contaminants in order to recalculate POPI and other pyrolytic parameters for use in characterizing and modeling of reservoirs that contain interfering OM that is not part of the migrated hydrocarbons, and therefore are not implicitly related to reservoir quality; and e. to provide a method for assessing hydrocarbon moveability and reservoir injectivity by the determination of drilling mud contamination as a means of assessing the displacement of reservoir fluids.

Definitions

As used herein, the following terms and designations have the meanings indicated HC—Abbreviation for hydrocarbons, THC is used for Total Hydrocarbons.

LV—Abbreviation for Alight volatile@ components. As used herein, LV refers specifically to the weight in milligrams of HC released per gram of rock at the initial static temperature condition of 180° C. (when the crucible containing the rock sample is inserted into the pyrolytic chamber) prior to the temperature-programmed pyrolysis of the sample.

TD—Abbreviation for "thermally distillable" components. As used herein, TD refers specifically to the weight in milligrams of HC released per gram of rock at a temperature between 180° C. and $T_{min}$(° C.).

TC—Abbreviation for Athermally crackable@ components. As used herein, TC refers specifically to the weight in milligrams of HC released per gram of rock at a temperature between $T_{min}$(° C.) and 600° C.

LV+TD+TC—Represents the total HC released between 180° C. and 600° C. in milligrams of HC released per gram of rock.

POPI—Abbreviation for the Pyrolytic Oil-Productivity Index. The POPI is calculated from the pyrolytic data by the following equation:

$$POPI = \ln(LV+TD+TC) \times (TD/TC), \text{ where ln is the logarithmic value.}$$

$T_{min}$(° C.)—The temperature at which HC volatilization is at a minimum between the temperature of maximum HC volatilization for TD and TC, and is determined where $\delta(HC)/\delta(T)=0$, and is negative before and positive after. Alternatively, a temperature of 400° C. can be used for samples where there is no discernable minimum between TD and TC. The latter type of samples generally have very low total HC yield.

Phi(φ)—The average porosity obtained directly from a rock sample or based on measurements by electric logs at a given depth.

$S_o$—The saturation of oil (volume/volume on a pore volume basis) either as calculated from electric logs by the Archie equation, or as determined from laboratory data by Dean-Stark analysis, or as by reference to the actual in-reservoir saturation that cannot be measured directly.

$S_w$—The saturation of water (volume/volume on a pore volume basis), either as calculated from electric logs by the Archie equation; or as determined from laboratory data by Dean-Stark analysis; or as by reference to the actual in-reservoir saturation that cannot be measured directly.

$S_{xo}$—The saturation of drilling mud filtrate and representative of the amount of HC displaced by the filtrate, and therefore, movable HC.

THC—Total hydrocarbons.

$AS_w$—The "apparent water saturation" as calculated from pyrolytic data.

Crucible—The stainless steel container in which the sample is pyrolyzed.

End Member ("EM")—A consistent type of organic matter or hydrocarbon that cannot be identified and distinguished by pyrolytic analysis.

Pyrolytic Characterizing Data (pcd)—Data values measured at a predetermined number of data points, each data point corresponding to a prescribed temperature.

OM—Organic matter, e.g., shale- and coal-like materials.

FID—Flame Ionization Detector

SUMMARY OF THE INVENTION

The invention comprehends novel methods for processing pyrolysis data from reservoir rock samples obtained from known locations under circumstances that are encountered during the drilling of wells to provide information that is important for the compositional modeling of the reservoir.

A first method is referred to herein as Compositional Modeling Method for Assessing Residual Hydrocarbon Staining, and provides a means of characterizing the relative contribution of end-member components to the overall pyrolytic response.

A second method that will be referred to as Method for Adjusting Pyrolysis End-Members is important for generating end-members that can be used in modeling, even when a pure end-member is not present in a particular data set.

A third method is referred to as Method for Assessing Pyrolytic Characteristics of Contaminants and provides a novel means for obtaining the characteristic pyrogram for organic components that occur in relatively low abundance in samples, but nonetheless are essential components for obtaining accurate modeling results.

A fourth method that will be referred to as Method for Adjusting Pyrolytic Parameters by Subtracting Contaminants is used to recalculate POPI and other pyrolytic parameters. It is especially useful for reservoirs containing interfering organic matter ("OM") that is not part of the migrated hydrocarbons to be assessed.

A fifth method referenced as Method for Assessing Hydrocarbon Moveability and Reservoir Injectivity, relies on utilizing all the above methods in order to obtain the best possible results of compositional modeling. This method relies on the detection of drilling mud contamination as a means for assessing the displacement of reservoir fluids and thereby assesses hydrocarbon moveability and reservoir injectivity. Significantly, the assessment of contamination through compositional modeling enables assessment of moveable hydrocarbons and reservoir injectivity in near "real-time", and can therefore provide this information before any other method currently known to the prior art.

A sixth method referenced as Method for Assessing Pyrolytic Characteristics of Ground Pollutants utilizes the characteristic pyrogram data for hydrocarbon pollutants known or believed to be present in soil and/or aquifers in a given region to characterize the relative contribution, if any, to the pyrolytic response of soil and aquifer samples tested.

BRIEF DESCRIPTION OF THE DRAWINGS

The invention will be further described below and with reference to the figures depicted in the attached drawings, where

FIG. 11, which is referred to in the specification as Table 1, is a reproduction for a hypothetical sample of the output file of a commercial pyrolysis instrument.

DETAILED DESCRIPTION OF THE INVENTION

The methods of the present invention have further developed capabilities of utilizing pyrolytic data in the characterization of hydrocarbon staining on rock samples that have been applied and proven in field tests to overcome the limitation associated with the prior art methodology of pyrolysis. This method has been developed using core samples from oil producing sites to model the composition of hydrocarbon staining in a system that had oil, tar and pyrobitumen. It was found that each of these components produced distinct "signatures" during pyrolysis and that these signatures can be associated with their pyrograms. Modeling the composition of hydrocarbon staining is accomplished by the mathematical recombination of varying amounts of the different components, by identifying the calculated curve from these possible components that achieved a Amatch@ with the actual curve generated from the data derived from the pyrolysis instrument.

The software developed to accomplish this matching for a group of samples includes the steps of analyzing the data and solving for a solution that achieves the lowest root mean deviation when comparing a calculated curve from the model to the actual output of the pyrolysis instrument. In a preferred embodiment, the analytical software was prepared utilizing the Microsoft Excel® program.

In the practice of the invention, it has been found preferable to provide a program that includes at least three components for the model systems. In an especially preferred embodiment of the invention at least four components and most preferably at least five components are provided in order to model the system for reservoirs where additional components are present.

In addition to adding characterizing data for other end-member components to the software, the capability to recalculate pyrolytic parameters based on removing one of the components constitutes a further aspect of the invention. This functional feature of the method of the invention can be applied as necessary in the assessment of apparent water saturation and POPI determinations in locations where a significant component of dispersed organic matter and coal material is present in productive reservoir rock.

I. Compositional Modeling Method for Assessing Residual Hydrocarbon Staining

Figure 1:
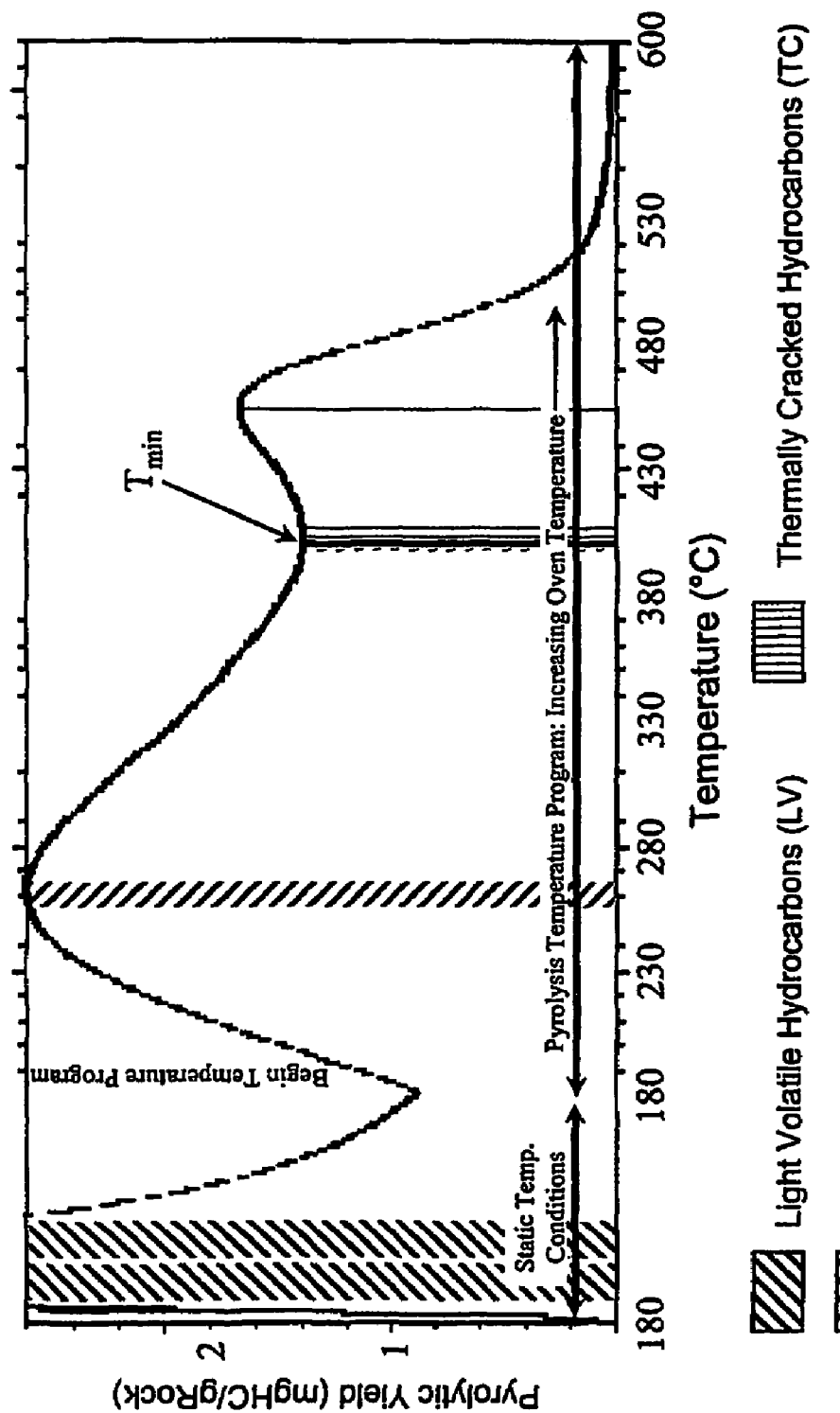
FIG. 1 is a typical output pyrogram from an instrument performing open-system temperature programmed pyrolysis.
Figure 2A:
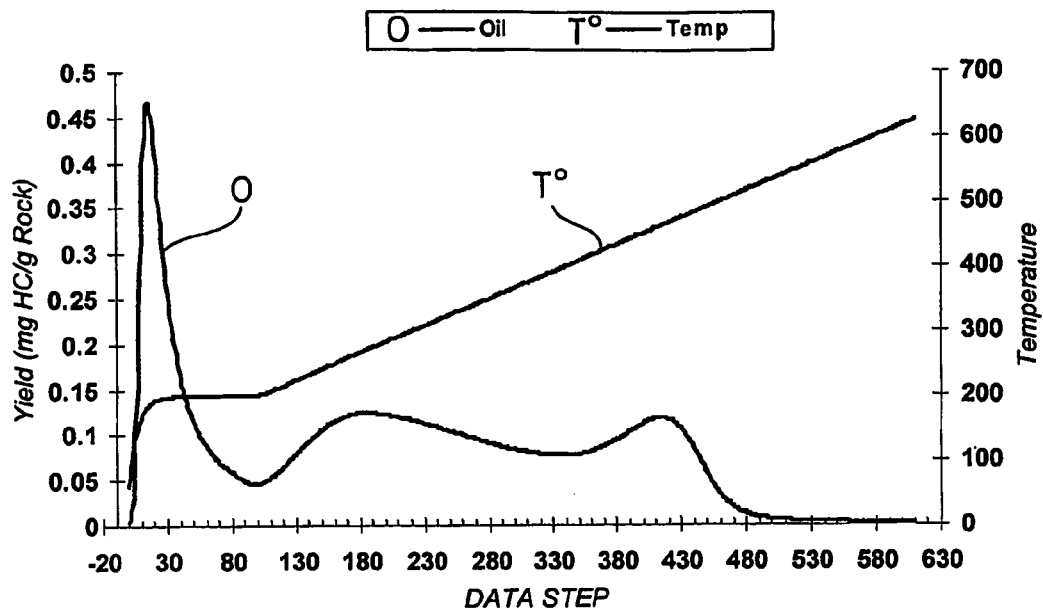
FIG. 2a is a typical pyrogram of API 30° oil from the K reservoir region.
Figure 2B:
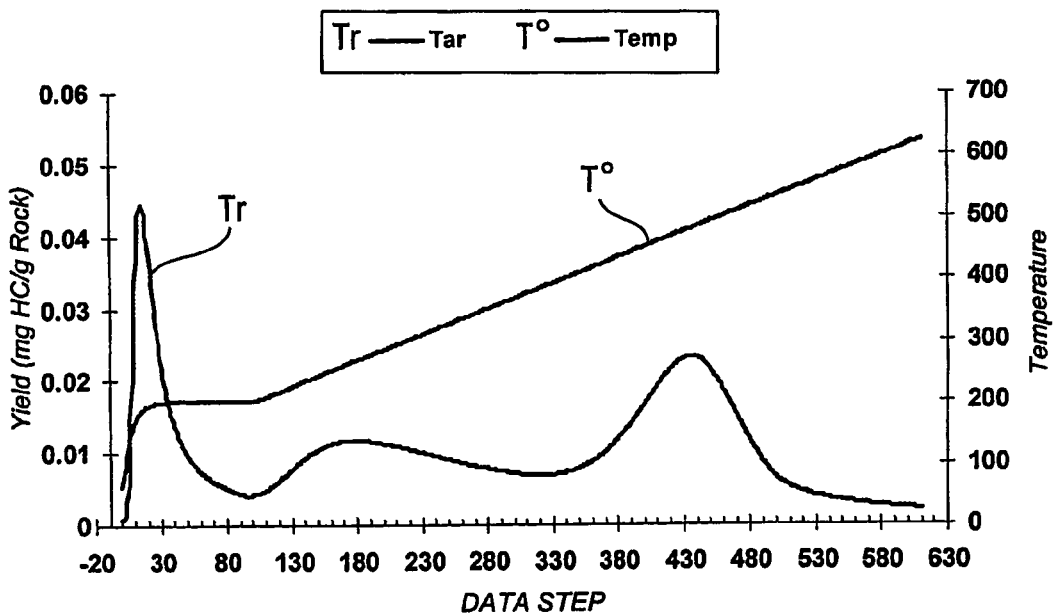
FIG. 2b is a typical pyrogram of tar from the K reservoir region.
Figure 2C:
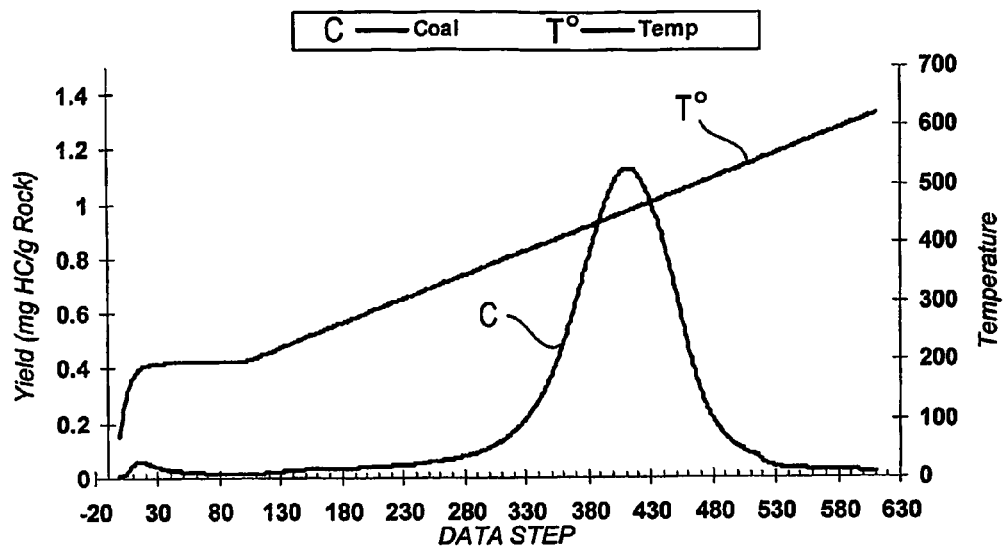
FIG. 2c is a typical pyrogram of coaly organic matter from the K reservoir region.
Figure 2D:
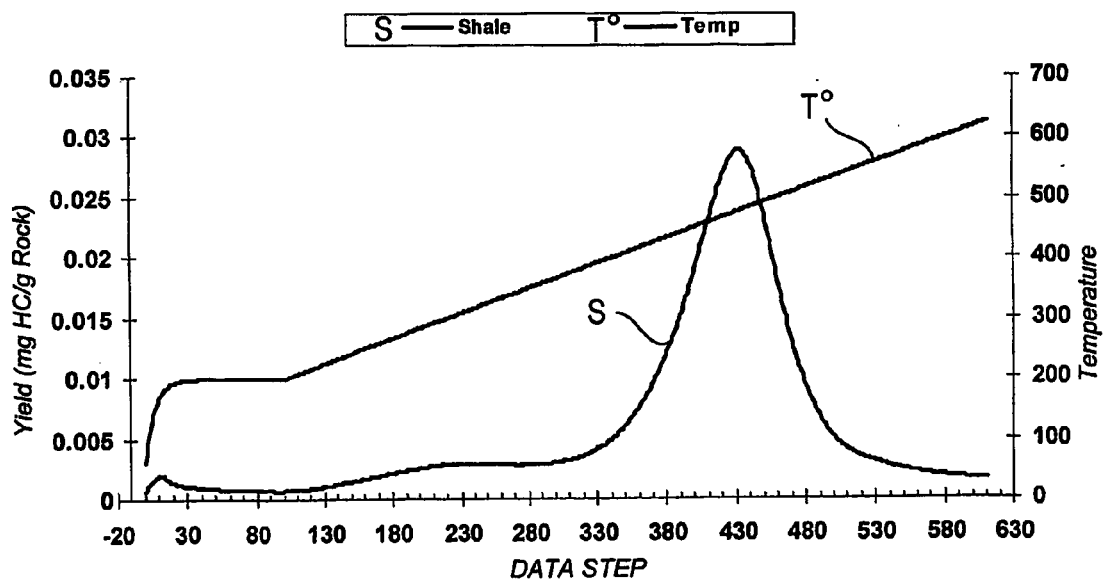
FIG. 2d is a typical pyrogram of organic-rich shale from the K reservoir region.

The Pyrolytic Oil-Productivity Index, or POPI, is based on two factors that are important in assessing whether or not oil-staining on reservoir rock is indicative of a productive reservoir. These factors are: (1) the amount of total hydrocarbon yield, and (2) the similarity of the hydrocarbon staining to the produced oils. Pyrolysis instruments are useful for quantifying the amount of hydrocarbon staining and the POPI method assesses the similarity to produced oils by subdividing the hydrocarbons into the Light Volatile (LV), Thermally Distillable (TD), and Thermally Crackable (TC) components (FIG. 1). However, it has been discovered that visual inspection of pyrograms also can be useful in assessing the type of hydrocarbons present because oil, tar, pyrobitumen, and other typical organic matter each also have very characteristic appearances.

FIGS. 2a through 2d are examples of pyrograms for samples with a nearly uniform composition of specific hydrocarbon or pyrolytically identifiable type of organic matter end-member components. These plots show the hydrocarbon yield on the y-axis for each data step that is recorded on the x-axis.

The number of data steps for a particular analysis can vary based on the type of pyrolyis instrument used. Two such commercially available instruments are Vinci's ROCK-EVAL™ and Humble's SOURCE ROCK ANALYZER™. The data that is obtained from the instrument and converted into a digital file can also vary. In the case description and examples that follow, the SOURCE ROCK ANALYZER™ was used and the data were output into digital form using a MICROSOFT EXCEL™ CSV file that recorded the yield and temperature over 611 data steps. The first 111 steps record the isothermal hold at 195° C. for 3 minutes and the next 500 steps record the programmed temperature run from 195° C. to 630° C. In general, the temperature associated with any specific step is the same from run to run, so that the step number can be associated with the temperature of the oven during the run.

Compositional modeling for a sample includes entering the yield at each individual data step as a value that is made up of the aggregate yield of the various end-member components. In this method, a specific and consistent temperature is associated with each step. The difference between the modeled yield calculated from the theoretical end-member component or components and the actual yield provides the basis for assessing whether a particular solution accurately reflects the actual composition in the reservoir rock sample.

Each such solution that is assessed must sum the difference between the calculated yield and the actual yield over all the data steps for the sample. Any of a number of statistical methods can be used in quantifying the overall error for any proposed solution. The modeling relies on iteratively varying the concentration of the various components until the aggregate error is minimized and the curves appear very similar. In one preferred embodiment the software utilizes the iterative process of proposing different compositions, calculating a hypothetical curve based on the yield at each data step, assessing the error for each particular solution, and then minimizing this aggregate error. These method steps can advantageously be completed by the use of macros and the Solver add-in application that is a standard component of the Microsoft Excel® program, and its use greatly automates the process. There are other software packages that can also be utilized to facilitate the methods used to model hydrocarbon composition are commercially available and include Corel Quattro Pro, Lotus 1-2-3, Corel Paradox, Lotus Approach, Microsoft Access and Microsoft Visual FoxPro.

Table 1, shown in FIG. 11, is the output file from a Humble SOURCE ROCK ANALYZER™ that has been converted to CSV format. The output data file records the same information in the same location for each sample tested and facilitates its extraction by spreadsheet data analysis programs. The header information at the very top of the report records the calculated parameters from the instrument and the run parameters. Starting at row 22, the instrument records the curve signal in the first three columns of the file. The first column contains the data step number, the second column records the signal from the flame ionization detector (FID) in milliVolts (mV), and the third column records the temperature of the oven associated with the data step.

In order to convert the output of the instrument into hydrocarbon yield using the instrument software, a known standard compound or composition from the reservoir region is analyzed. With the data from the standard, the instrument can calculate the conversion factor (CF) to relate millivolts from the FID to hydrocarbon yield in units of milligrams per gram of rock (gRock). From the data file, these conversion factors are calculated for each sample by summing the total signal in column two and then dividing this signal by the total hydrocarbon yield of the sample in accordance with the following mathematical expression:

$$CF_{FID} = [\Sigma Signal_{step\ 1-611}(mV)] / [(LV+TD+TC)(mgHC/gRock)] \quad (1)$$

The signal that is taken for any particular data step is then be converted into mgHC/gRock by simply dividing the signal by CF:

$$Yield_{step\ X}(mgHC/gRock) = [Signal_{STEP\ X}(mV)] / [CF_{FID}(mV/mgHC/gRock)] \quad (2)$$

In a preferred embodiment, all instrument output is converted into yields for the purpose of making the relevant calculations to combine end-members (EM) and to compute the results based on modeled solutions. This is done because the actual yield that is given for each end-member sample and for each sample that is being modeled will be unique. In order to model the relative composition of end-members that make up a particular sample, the data for each end-member is normalized so that the total hydrocarbon yields of each recalculated end-member is the same as the actual sample. Therefore, the quantity of an end-member component that would be present for a pure end-member having the same yield as the sample can be expressed as follows:

$$Yield = [Yield_{EMSTEPX}] * ([Total\ Yield\ (THC)Sample] / [Total\ Yield\ End\text{-}Member]) \quad (3)$$

In the above equation and those that follow the "*" notation is used to indicate multiplication.

This equation is used to calculate the aggregate yield that would be found for a hypothetical sample that contained various percentages of end-members that are needed to describe the sample behavior. Thus, the calculated yield for a proposed hydrocarbon composition at any given data step is the sum of the percentages of each end-member (% $EM_{1\ to\ 5}$) divided by 100 and multiplied by the yield of the end-member at step x ($Yield_{EM1\ to\ 5,X}$) times the ratio of the total yield of the sample divided by the total yield of the end-member ($THC_{sample}/THC_{EM1\ to\ 5}$). This step can be expressed as follows:

$$\begin{aligned}Calculated\ Yield_{EM\ 1-5,X} &= (\%\ EM_1/100)*Yield_{EM1,X}* \\ &\quad (THC_{sample}/THC_{EM1}) + (\%\ EM_2/100)* \\ &\quad Yield_{EM2,X}*(THC_{sample}/THC_{EM2}) + \\ &\quad (\%\ EM_3/100)*Yield_{EM3,X}* \\ &\quad (THC_{sample}/THC_{EM3}) + (\%\ EM_4/100)* \\ &\quad Yield_{EM4,X}*(THC_{sample}/THC_{EM4}) + \\ &\quad (\%\ EM_5/100)*Yield_{EM5,X}*(THC_{sample}/THC_{EM5})\end{aligned} \quad (4)$$

The error between a particular modeled solution for Step X and the actual analytical result for Step X can be obtained by simple difference. However, since some of these values will be positive and some negative, the treatment of errors for all values calculated, e.g., Steps 1-611, is easier to accomplish through the application of a root mean squares (RMS) calculation. Other statistical treatments would also achieve the same results if they were to employ the difference between each modeled yield and actual yield as an absolute value.

In one preferred method, the RMS average difference is calculated in terms of a percentage that relates to the total response of the sample and can be expressed as follows:

$$\% \text{ RMS}_{CALC\ vs\ ACTUAL} = 100 * ((\text{AVERAGE}_{STEP, 1-611}(\text{Yield}_{CALC} - \text{Yield}_{ACTUAL})^2)^{1/2} / (\text{AVERAGE}_{STEP, 1-611}(\text{Yield}_{ACTUAL}))) \quad (5)$$

The modeling process comprises the steps of varying the percentage of the end-members that are present in the system ($EM_{1-5}$ are preferably used) until the calculated curve matches the actual curve and the % RMS error is minimized. Due to the fact that so many calculations must be made to assess any solution, the use of a spreadsheet program to perform these calculations and automatically plot the result that is achieved greatly simplifies the process. Moreover, a software application such as Solver that is present as an add-on in Microsoft Excel®, can greatly expedite the data processing capability of iteratively solving problems with multiple variables that seek to converge on a desired solution which in this case is minimizing error.

Figure 3:
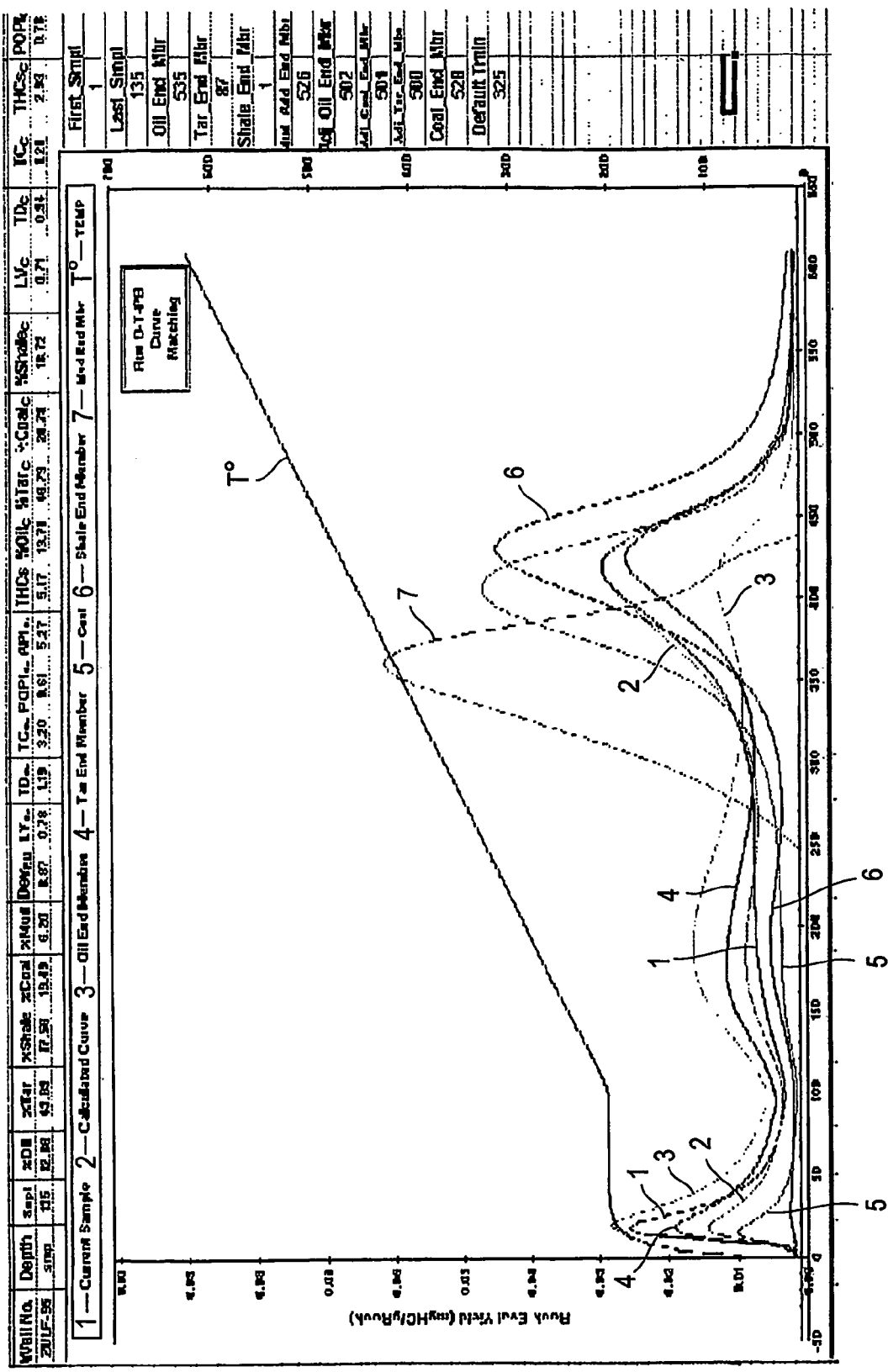
FIG. 3 is a plot showing the compositional modeling interface that was developed to perform the calculations, where the plot shows pyrograms associated with the current sample, the calculated solution and the end-members that are used in the modeling process.
Figure 4:
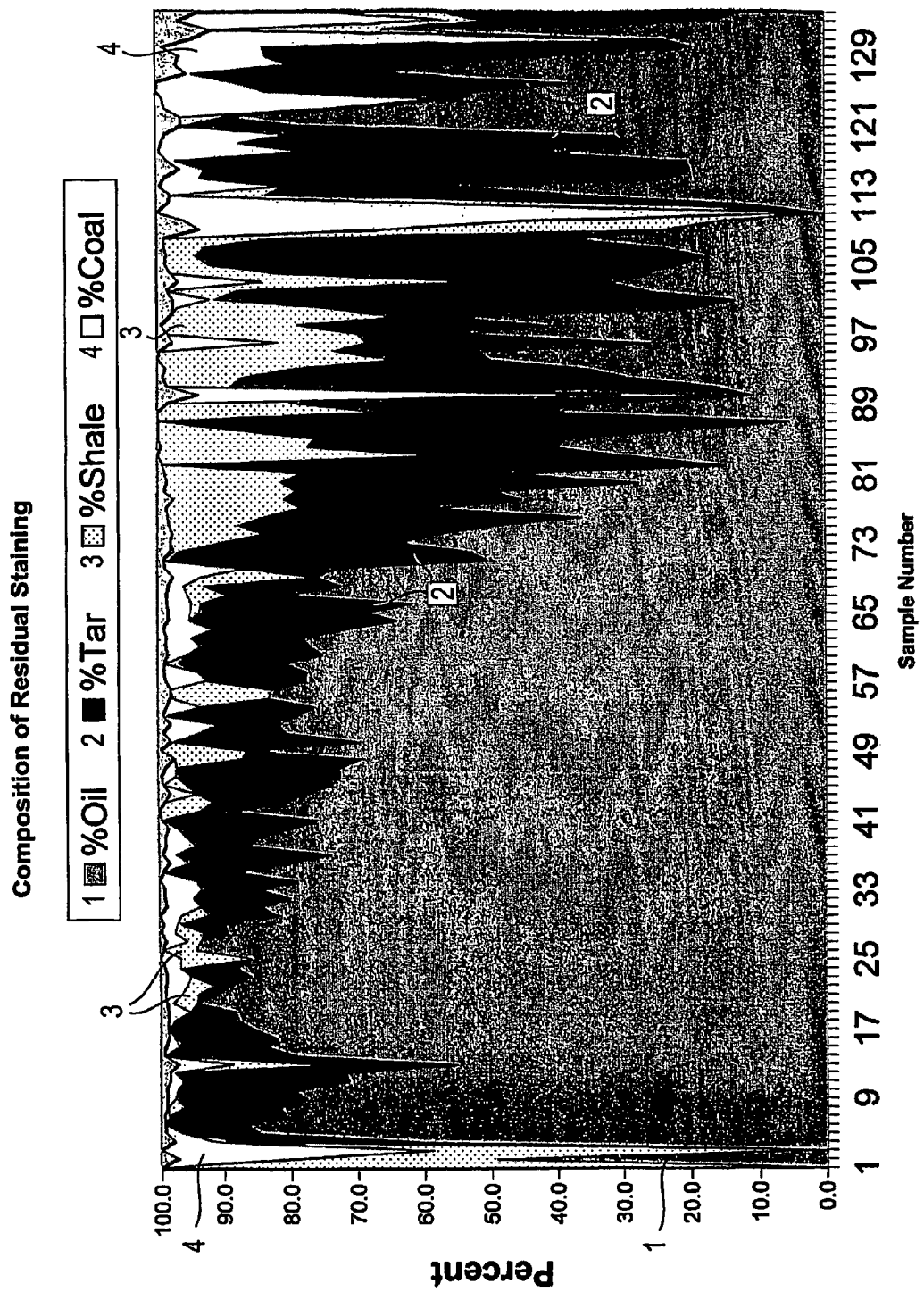
FIG. 4 is the resultant compositional modeling for well Z-95 showing the percentage of oil, tar, shaley OM and coal present in reservoir rock samples.
Figure 5:
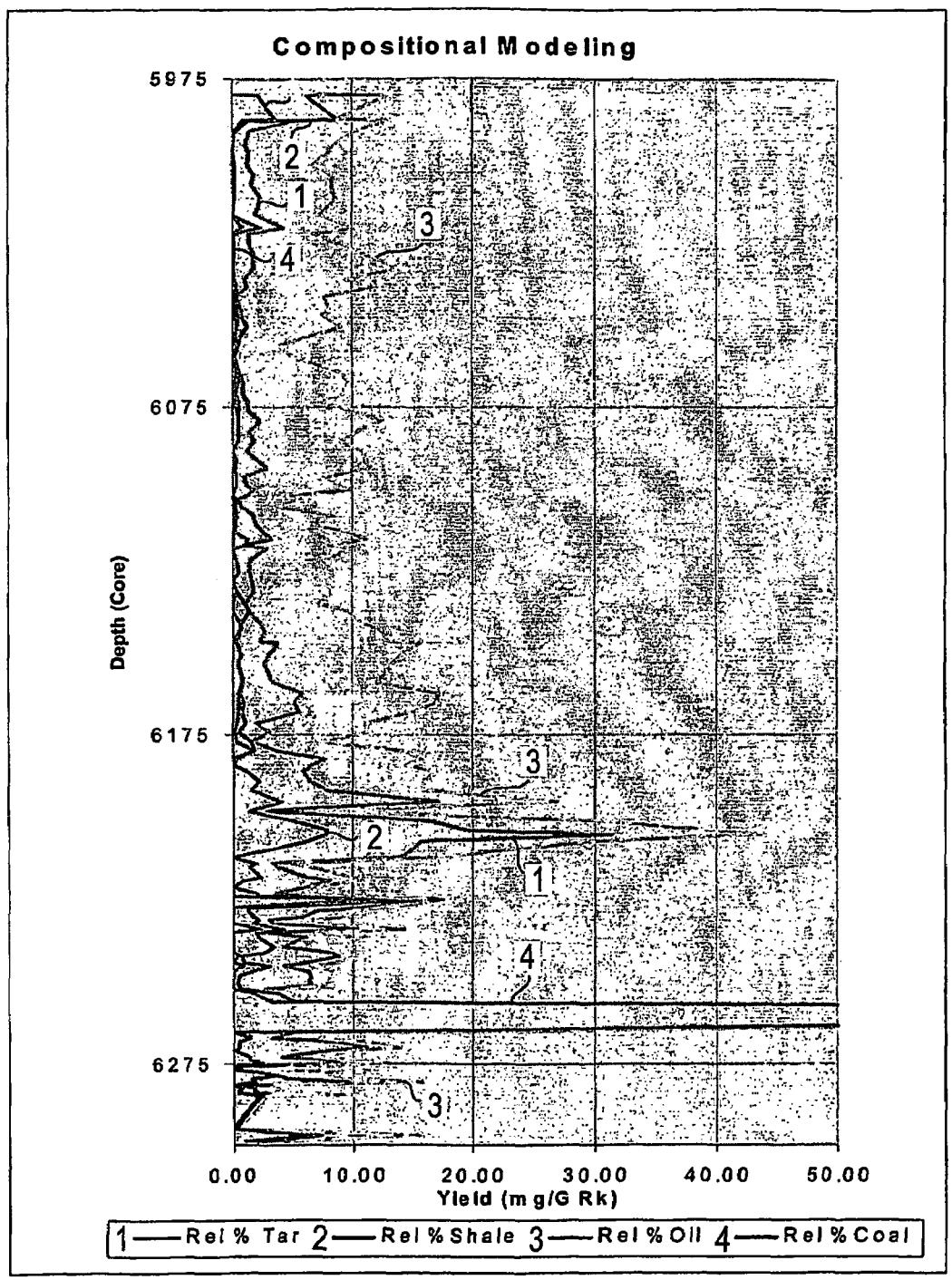
FIG. 5 is the plot resulting from the compositional modeling of well Z-95 showing the relative pyrolytic yield of oil, tar, shaley OM and coal present in reservoir rock samples and demonstrates how hydrocarbon yield increases significantly in true tar mats or coal beds.

FIG. 3 shows the graphic interface that was utilized for a five end-member component systems at well-site Z. The graphic illustration includes curves for the current sample, the calculated solution based on the percentage of the components, the oil end-member, the tar end-member, the shale end-member (typical of dispersed kerogen found in shaley lithologies), the coal end-member, and the drilling mud end-member (contamination). The parameter listed on the top line as $\text{DEV}_{RM}$ is the RMS deviation as a percent of total yield and is the value that is minimized in obtaining a reasonable solution for a given sample. When all samples are analyzed for a particular well, the results can be plotted as in FIG. 4 to reveal how the composition varies throughout the sampled section. Plots such as this are very useful in identifying important trends, such as increasing tar, or in identifying individual coal or tar units that may have important implications in reservoir performance. An alternative method of presenting the data that is shown in FIG. 5 is to plot the relative contribution of each EM component by depth with each curve being adjusted for changes in yield in the samples. This type of plot is particularly useful for identifying true tar mats that typically have an associated dramatic increase in hydrocarbon yield as opposed to a change in composition that appears to be tar, but is present in relatively low concentrations and not likely to affect reservoir performance.

II. Method for Adjusting Pyrolysis End-Members

One problem that is encountered in this application is the lack of true end-members in a given sample set. In fact, even in the best examples, small adjustments to an end-members composition may be required to optimize the modeling process. For example, a sample that is from an oil reservoir may consist of mostly tar or pyrobitumen. However, due to its direct contact with the hydrocarbon column, there is a substantial amount of oil staining present in the sample. In most cases, this oil is not producible, but removing its presence from an end-member is desirable.

Figure 6:
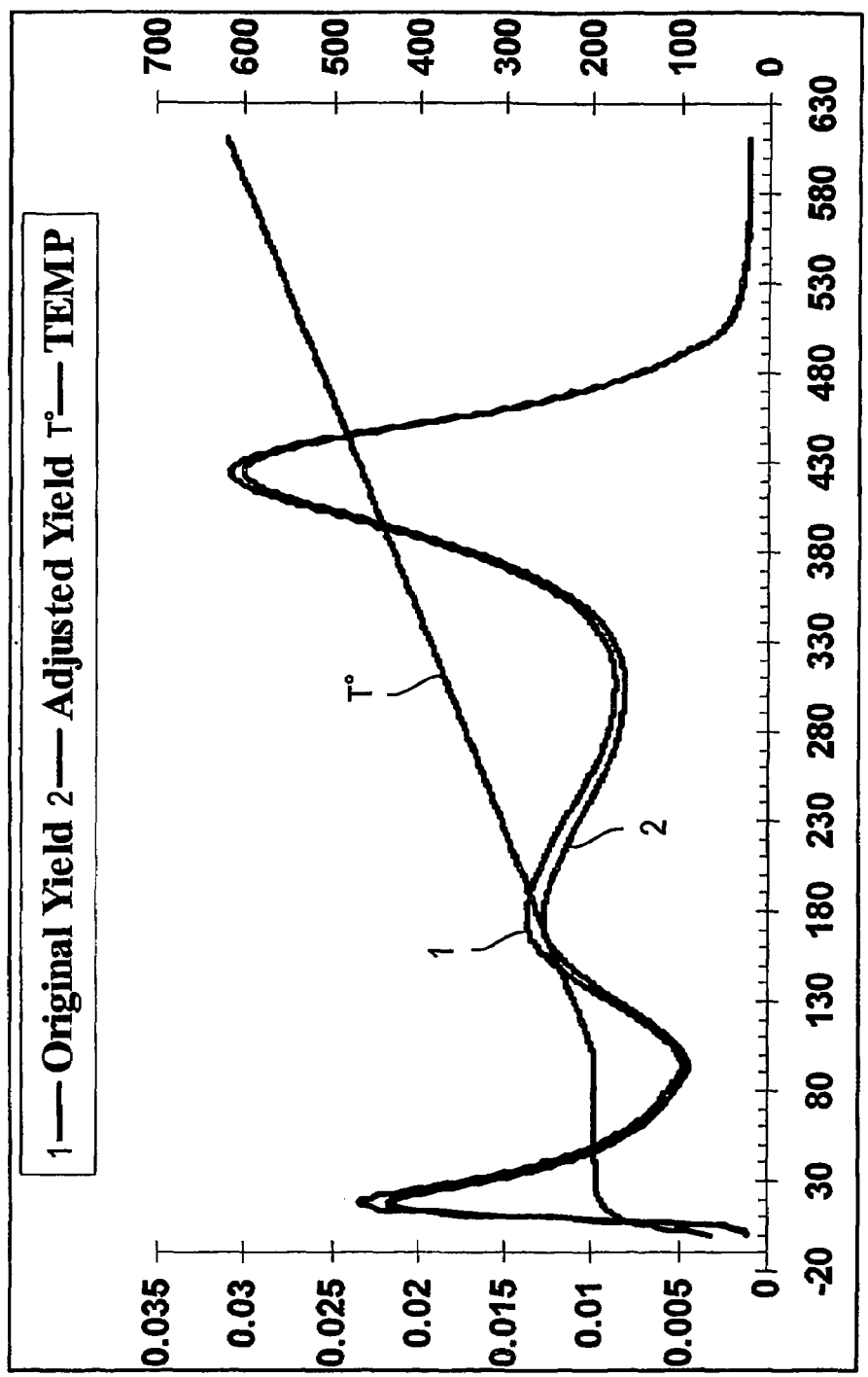
FIG. 6 is a plot of pyrolysis curves showing the original yield for a tar end-member sample and the resultant adjusted curve that is obtained by subtracting 5% oil from the sample.

FIG. 6 shows the result from removing a minor component of oil from the tar end-member used for modeling at Z. The same approach may be used to remove up to 30% of a component without adversely affecting the modeling process. However, the greater the adjustment needed, the more effort that should be devoted to finding a better end-member. This can often be augmented by additional laboratory analyses that help to confirm the composition of the staining, particularly when there are insoluble organic components such as shales and coals present in samples. The equation to accomplish the subtraction of one end-member ($EM_1$) from another end-member ($EM_2$) to form a better or adjusted end-member from $EM_2$ is found by taing the yield from the end member that is being adjusted and subtracting from it the percent of the end-member to be subtracted divided by 100 and multiplied by the yield of that end-member times the ratio of the total yield of the end-member to adjust divided by the end-member to subtract. This step can be expressed mathematically as follows:

$$\text{Adjusted Yield}_{EM2,\ STEP\ X} = \text{Yield}_{EM2\ STEP\ X} - (\% \text{ Sub}_{EM1}/100) * \text{Yield}_{EM1,X} * (\text{THC}_{EM2}/\text{THC}_{EM1}) \quad (6)$$

The resultant curve that is generated by applying this equation over all the data steps that are present is then used to recalculate all the pyrolytic parameters in order to thereby provide a basis for assessing the appropriateness of the adjustment. When the adjusted or recalculated data for the pyrolytic parameters is deemed favorable, it is used as an end-member for modeling the composition of other samples.

III. Method for Assessing Pyrolytic Characteristics of Contaminants

As stated above, end-members can be adjusted when they contain up to 30% of a component that is different from the desired end-member needed for input into the modeling analysis. The end-members previously described are the types that occur in reservoir rocks and make the application of this assumption reasonable. However, it has been found that significant contamination is often observed when pyrolytic analysis is undertaken at well sites, and the effects can obscure and adversely effect the interpretations that are made. Typically, these contaminating components do not constitute a pure mixture in any given sample, i.e., they are usually present as less than 30% of the total yield.

Efforts have been made to assess drilling mud contaminants based on analysis of dried drilling mud samples. However, contrary to what would ordinarily be expected, pyrograms obtained from these samples were not successful as input into the compositional modeling process. Rather, it has been discovered that the resultant contaminant found on the samples is typically a residual component that is influenced by the drilling conditions, sample collection methods, and the sample washing and preparation processes utilized. Experience has shown that the appearance of the contamination is usually quite distinct from organic matter that is indigenous to the reservoir rocks being analyzed, but that a single end-member sample cannot be obtained.

Wellsite operations have focused on horizontal wells, where the lithologic changes occur gradually because most important changes in reservoirs occur in the vertical section and only change slowly in lateral directions. One assumption tested was that a consistent contamination level would be present in all samples and that this uniform level could be subtracted from all results. However, data analysis from drilling wells show that the amount of contamination varies significantly from sample to sample.

The novel method of the present invention that allows the assessment of background contamination relies on the variable contamination level in combination with gradual lateral changes in a reservoir. It has been determined that adjacent samples are typically similar and vary only in the amount of a clearly discernable contamination component.

The method of the invention consists of comparing adjacent samples that have a character indicating that contamination is present from drilling mud, adjusting the curves so that they have the same total yield, and then subtracting the curve with lesser contamination from the one that has more. The results can be improved by successively averaging the output from this method over several different sets of samples that are compared for contamination. The resultant yield from this step-wise process is then used in the modeling process to define drilling mud contamination as another end-member.

Figure 7:
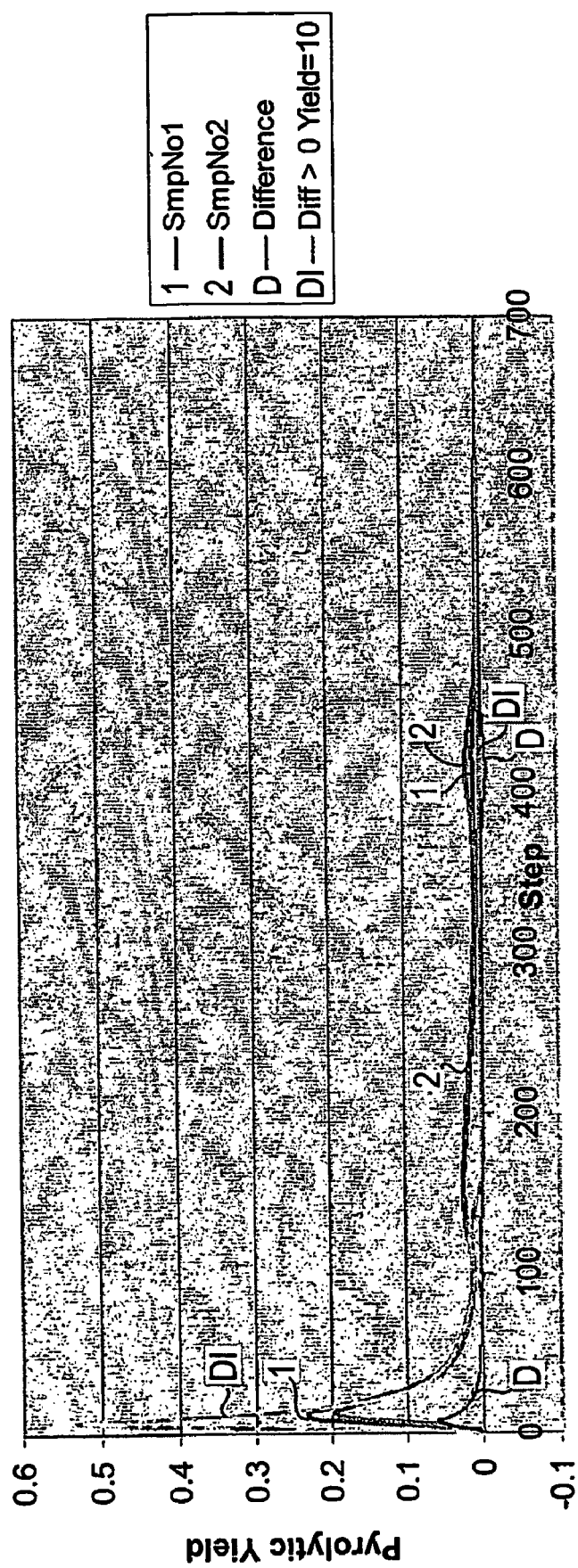
FIG. 7 is a plot of contaminant assessment for use in compositional modeling, where the first sample has greater contamination from diesel that is added to increase mud lubricity and the adjacent second sample has lesser contamination; the difference between the curves, and the resultant curve that is used in compositional modeling are also plotted, all being adjusted to have a yield of 10 mgHC/gRock for plotting convenience and utilizing only positive differences, truncating data that is negative.
Figure 8:
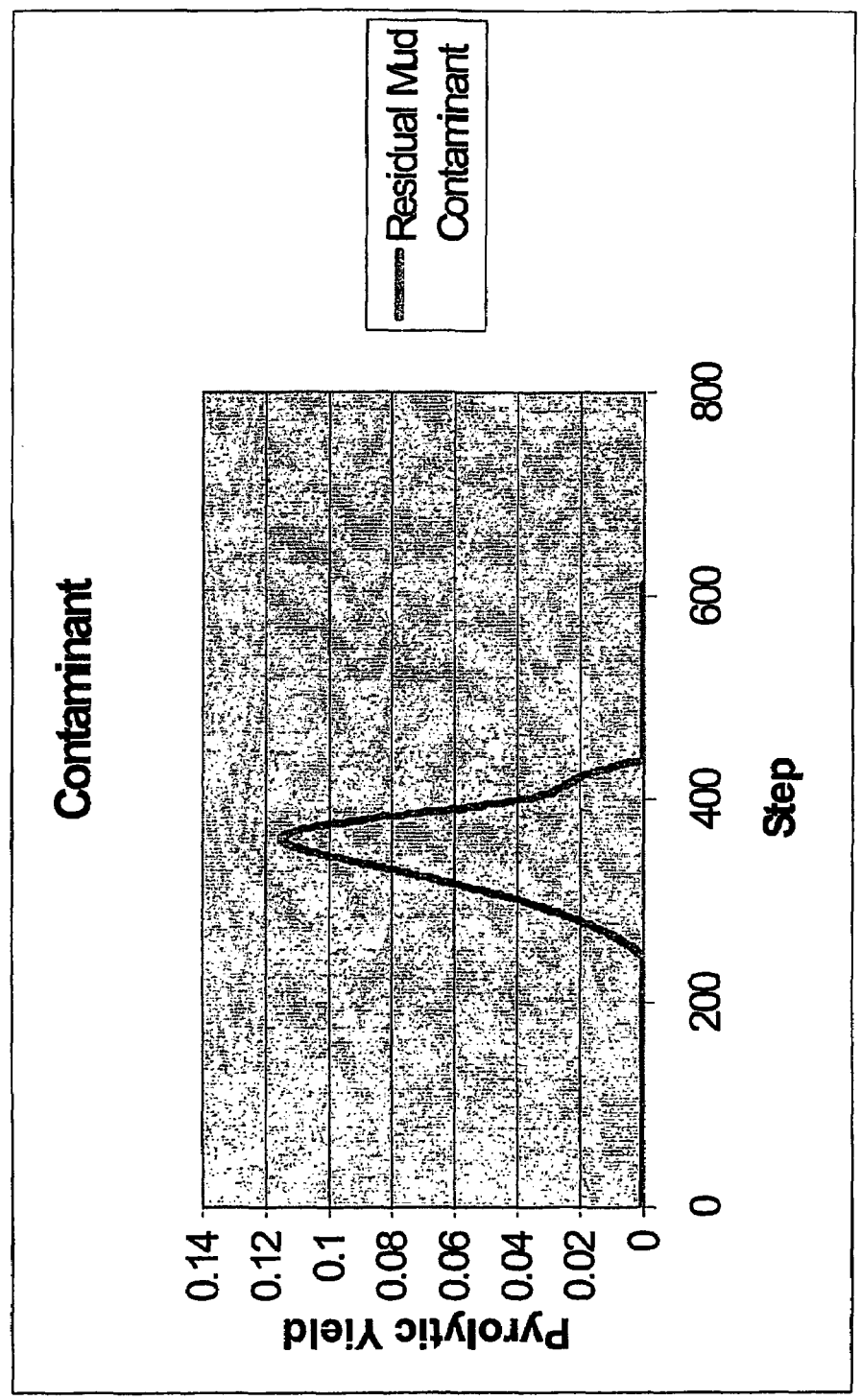
FIG. 8 is a resultant plot of contaminant assessment for a second residual contaminant that is typically associated with drilling operations in the Q reservoir region and is therefore useful as an end-member for compositional modeling.

FIG. 7 shows the results derived from applying this process on mud-additives from from a wellsite at Q. The contaminant present in these samples is diesel oil that was added to increase drilling mud lubricity. The dark blue curve is the curve from the sample with greater contamination and the magenta curve is an adjacent sample with lesser contamination. The green curve is the difference between the curves, and the light blue curve is the resultant curve that is used in compositional modeling for this site. In a preferred embodiment, the curve is adjusted to have a yield of 10 mgHC/gRock, which makes it convenient for plotting, because the adjusted curve utilizes only positive differences and truncates data that are negative. An example of another typical contaminant that is seen from residual mud in drill cutting samples from well site Q is shown in FIG. 8.

Mathematically, the subtraction of the two curves is accomplished by taking the value of the yield at each data step from the curve with greater apparent contamination and then subtracting the product of the yield from the associated data step from the sample with lesser contamination and then multiplying by the ratio of the total yield of the first sample to the second sample that has lesser contamination. The stepwise process can be expressed mathematically as follows:

$$\Delta Yield_{smpl1, smpl2, STEP\ X} = Yield_{smpl1STEPX} - Yield_{smpl2STEPX} * (THC_{smpl1}/THC_{smpl2}) \quad (7)$$

IV. Method for Adjusting Pyrotytic Parameters by Subtracting Contaminants

In applying the methods from compositional modeling, any given sample will have three pyrograms to be concerned with: (1) the actual data from analysis, (2) the calculated pyrogram that is reconstructed from the addition of the end-member components in proportion to the best fit solution for the sample, and (3) the corrected pyrogram that is a result of taking the actual pyrogram and subtracting background material that is either not part of the indigenous hydrocarbon staining, such as contamination, or is interfering organic matter like coal and disseminated organic matter that also is not associated with the migrated hydrocarbons that are being assessed. The so-called background material can also include residual tar components that are attributable to an earlier hydrocarbon charge, but that is not detrimental to reservoir performance.

The methods for producing the data to generate the calculated or corrected pyrogram from the end-member components has been described above and is a necessary step in determining the appropriateness of any particular solution that is arrived at through the modeling process. However, the corrected pyrogram or curve is calculated from the actual pyrogram by first modeling the composition of the sample, subtracting the components that are contaminants or that are otherwise interfering with interpretation from each data step, and then re-calculating the pyrolytic parameters LV, TD, TC and $T_{min}$; the final step is the recalculation of all other values of interest.

Figure 9:
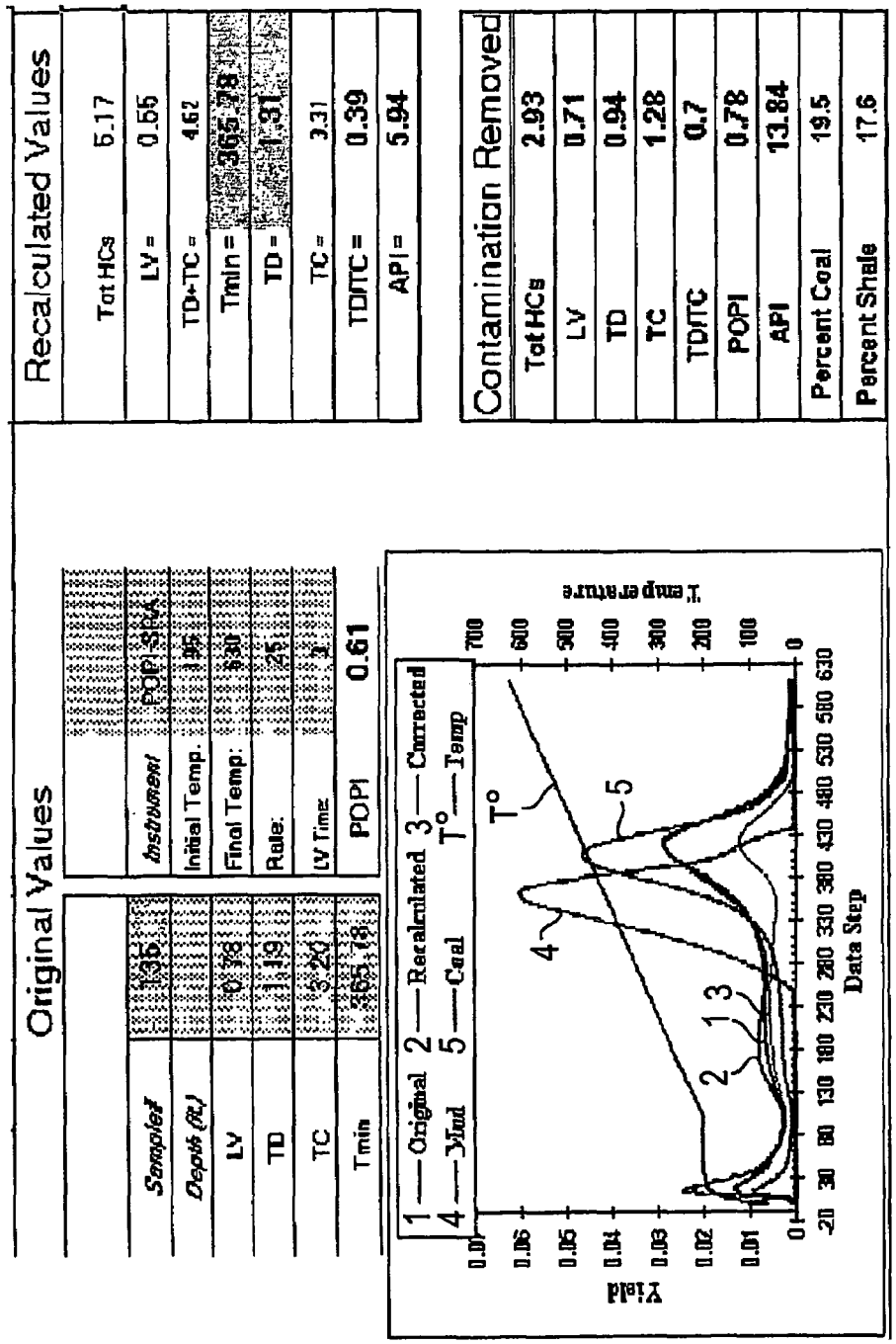
FIG. 9 is a plot showing an example of compositional modeling applied to recalculate values based on modeled percentages of end-member components and recalculated results that have removed the effect of interfering contaminants.

FIG. 9 is a graphic display of the interface that accomplishes this recalculation for a well identified as Z-95. In this example, the effects of shaley OM and coaly OM as determined by compositional modeling have been removed from the actual data (the dark blue plot) and to produce the resultant corrected curve (the light purple plot). For any given data point or step X that has interfering components $EM_1$ and $EM_2$, the corrected yield can be calculated as follows:

$$Yield_{Corr} = Yield_{STEPX} - ((\%\ EM_1/100) * Yield_{EM1,X} * (THC_{sample}/THC_{EM1})) + (\%\ EM_2/100) * Yield_{EM2,X} * (THC_{sample}/THC_{EM2})) \quad (8)$$

V. Method for Assessing Hydrocarbon Moveability an Reservoir Injectivity

Initially the major concerns and challenges of employing pyrolytic methods in the field at well drilling sites were focused on removing the effects of drilling contaminants in order to see the true character of the residual hydrocarbon staining present on the rock samples. This step was necessary in order to utilize the pyrolysis data to direct the placement of horizontal power water injection wells that were to be drilled in the oil-water transition zone. Due to this placement, previously developed methods such as the POPI method and Apparent Water Saturation method were anticipated to be less than optimal. However, since an initial requirement is the identification of tar, the use of pyrolysis was expected to provide useful information since pyrolysis can quantify the amount of tar present and thereby assist in assessing reservoir injectivity. The method was determined to be an important tool for reservoir characterization in high-risk areas for tar occurrence. The reliability of this method has been demonstrated in the field by the results of numerous well drillings.

The compositional modeling method of the invention provides characterization and quantification of the residual hydrocarbon staining as a means of assessing tar occurrence and reservoir injectivity.

Although it might seem logical that the effect of contamination on the data would be consistent (because the composition of drilling mud remains relatively constant or changes slowly during the drilling process) and therefore relatively straight forward to remove, it was found to be highly variable. Moreover, simple correction of the data to remove this effect did not increase sensitivity as anticipated. When the modeling of contamination was pursued, it was discovered that by plotting the contamination alongside well log data, as one of the modeled components, the amount of contamination seemed to be much greater in the portions of the reservoir that had more favorable reservoir rock. In most cases, portions of reservoirs that appear to be very unfavorable for fluid moveability (e.g., tight rock), do not exhibit a significant amount of contamination in the drill cuttings analyzed.

The explanation for these observations is that in favorable reservoir rock that contains either moveable hydrocarbons or is injectable for water, the process of drilling will typically result in displacement of the reservoir fluid by drilling mud. If a rock is of poor reservoir quality, the drilling mud may coat the surfaces of the cuttings' but it will not enter the pore space and will be easily washed away during sample preparation. Contamination is therefore observed to a much greater extent when mud invades pore space and cannot be washed away. This phenomenon has been recognized in connection with the assessment of moved hydrocarbons using resistivity logs. As is known to those of ordinary skill in the art, the invasion of mud filtrate disturbs the resistivity profile and therefore can be of assistance in characterizing the reservoir rock. The modeling of contamination present in drill cuttings through the compositional modeling method of the invention provides a means of assessing the invasion of drilling mud into reservoir rock pore space and can be similarly utilized in data analysis and modeling. It is to be noted, however, that the pyrolysis data method provides a completely independent assessment of this important characterizing parameter.

Furthermore, there is currently no means in the oil industry for assessing moved hydrocarbons in "real time" because doing this through resistivity logging demands that sufficient time shall have lapsed so that an invasion profile may develop. Typically, this requires eight or more hours. The assessment of contamination through the compositional modeling method of the present invention provides the capability for making this assessment in less time than required by any other method that is now known to be available to the industry. Moreover, the method also has the capability of optimizing the placement of horizontal power injector wells, as it is applicable to reservoir rock that is in the oil-water transition zone where POPI and Apparent Water Saturation are less sensitive indicators of reservoir performance.

Figure 10:
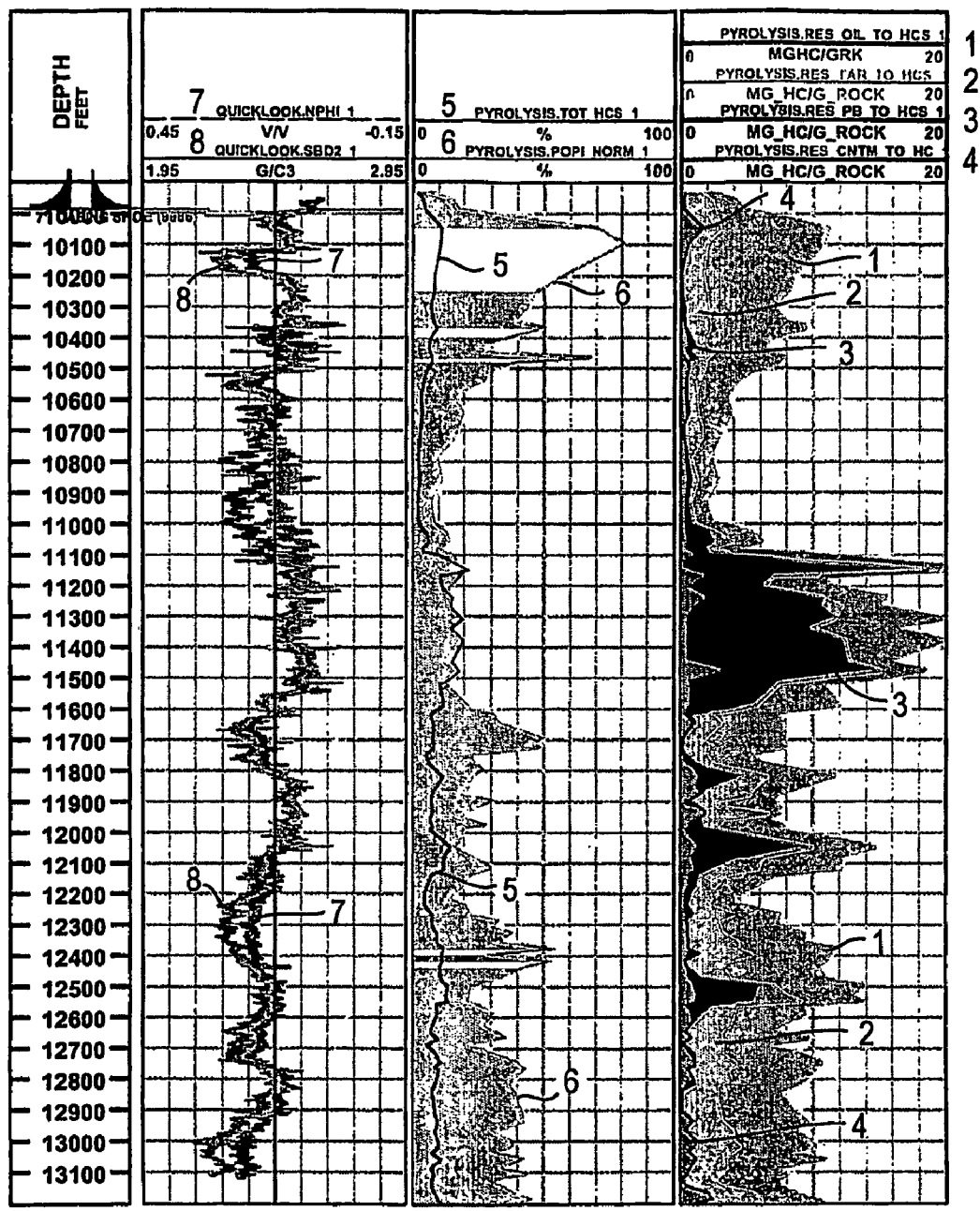
FIG. 10 is a composite plot of well log and pyrolysis data generated in the field for well Q-539 that shows a good correspondence between the zones with greatest porosity and highest residual drilling mud.

Referring to FIG. 10, there is shown a composite plot of well log and pyrolysis data generated in the field for welisite Q. The data show a good correlation between the zones with greatest porosity and highest content of residual drilling mud. Some minor shifting of boundaries is present due to caving of drill cuttings, but the assessment of residual drilling mud correlates well with the prior art means of assessing reservoir quality.

We claim:

1. A method of identifying the relative proportions by percent of a plurality of end member components in a sample of reservoir rock taken from a specific oil field by analysis of pyrolytic characterizing data (pcd), the method comprising the steps of:
   a. identifying the end-member components known to be present in reservoir rock in the oil field;
   b. preparing individual pyrograms consisting of pcd for each of the components identified in step (a);
   c. storing the pcd for each component in a digital data file;
   d. conducting a pyrolytic analysis of a sample from the oil field of reservoir rock that contains one or more hydrocarbon and organic matter components of the type identified in step (a) to obtain pcd for the sample;
   e. comparing the pcd for the sample with the pcd obtained in step (b) for each of the components, measuring and recording the difference between the sample pcd and the pcd for each of the components;
   f. applying a statistical analysis to minimize the aggregate differences between the pcd for the sample and a combination of pcd selected from the components;
   g. recording for retention and display for analysis the resulting pcd that constitutes the minimum aggregate error over the temperature range of the pyrolytic analysis; and
   h. analyzing the displayed data to identify the respective components.

2. The method of claim 1, wherein the pyrolytic analysis is conducted over a temperature range of from about 180° C. to about 700° C.

3. The method of claim 2, wherein the pcd is comprised of a predetermined number of data points based on temperature, and the pcd of the sample and each of the plurality of end member components is compared at each data point.

4. The method of claim 3, wherein at least a portion of the data points are at intervals of one degree Centigrade or less.

5. The method of claim 1, wherein the pcd in step (g) is recorded in a form for visual analysis selected from the group consisting of pyrogram displays and tabular data.

6. The method of claim 1, wherein the analytical method is selected from the group consisting of the method of least squares and root mean squares.

7. The method of claim 3, wherein there are 611 data points and the method includes the further steps of converting the pcd to hydrocarbon yield per gram of sample, gRock, at each data point by applying a conversion factor, CF, the conversion factor being calculated for the 611 data points as follows:

$$CF_{FID} = \frac{[\sum Signal_{step1-611}(\text{mV})]}{[(LV + TD + TC)(\text{mgHC}/\text{gRock})]}$$

where mV is millivolts and the other terms of the equation are as defined above; and recording the conversion factor in a data file.

8. The method of claim 7 which further comprises determining for a predetermined data point X, the yield, $Yield_X$ in accordance with the following:

$Yield_x(\text{mgHC/gRock}) = [Signal_{STEPX}(\text{mV})] / [CF_{FID}(\text{mV/mg HC/gRock})]$ 9. The method of claim 8 which includes the step of normalizing the pcd for each selected end member component, EM, for comparison to the pcd of the rock sample as a pure component at a data point X, the normalized yield being calculated as follows:

$$Yield = Yield_{EMX} \times \frac{\text{Total Yield}(THC) \text{ Sample}}{\text{Total Yield Component } EM}$$

where $Yield_{EMX}$ is the yield of the selected end member at data point X; and recording the results of each calculation in a data file.

10. The method of claim 1, wherein the number of end member components is five.

11. The method of claim 1 in which steps (d)-(h) are repeated for a plurality of samples taken from different known positions in a selected section of the reservoir formation.

12. The method of claim 11 in which the data from step (g) for each sample is plotted to display variation in composition in the section selected.

13. The method of claim 12, wherein the data from step (g) for each sample is plotted to display for analysis the relative contribution of each component by depth and each curve is adjusted for relative yield in total hydrocarbon.

14. A method of adjusting the quantitative contribution of a first minor end member component, EM1, in a component set containing y end members, where y is from 3 to 5 components, the method comprising the steps of:
   a. selecting a second end member component EMy-1;
   b. determining the yield of EM1 and selecting a percentage Z % of EM1, $Z\%_{EM1}$, by which EM1 is to be reduced;
   c. applying the following calculation for each one of a plurality of data points X:

$Adjusted\ Yield_{EMy-1(x)} = Yield_{EMy-1} - Z\%_{EM1} \times Yield_{EM1}(x) \times THC_{EMy-1} 100 THC_{EM1}$ d. applying the adjusted yield for component EM2 to each of the data points to recalculate a resultant pcd of the component and recording the results; and e. comparing the resultant pcd to the pcd of the sample to provide the best fit of the data.

15. A method for identifying the presence of drilling mud contaminants in reservoir rock samples recovered from a well bore during drilling of the well, where the rock samples are subjected to pyrolytic analysis, the method comprising the steps of:

a. providing a plurality of samples of reservoir rock removed from spaced-apart adjacent locations along the well bore;

b. subjecting the rock samples to pyrolytic analysis to obtain pcd consisting of a plurality of data points for each of the plurality of samples obtained in step (a);

c. adjusting the pcd so that all samples have the same total yield of hydrocarbons;

d. subtracting the pcd for a first sample having apparent contamination multiplied by the ratio of $$\frac{THC_{smp}X}{THC_{smp}X+1}$$

from the pcd of a second adjacent sample having greater apparent corresponding contamination at the plurality of data points; and e. recording for analysis a new adjusted contamination pcd based upon step (d).

16. The method of claim 15 which includes the further step of converting the adjusted contamination pcd of step (d) to have a yield of 10 mgHC/gRock.

17. The method of claim 15 which includes the further step of displaying for analysis a graphical plot of the contamination curves of pcd for pairs of adjacent rock samples and the resultant apparent contamination pcd obtained in step (d).

18. The method of claim 15 which further comprises the step of averaging the output of step (d) over at least one additional pcd obtained from other reservoir rock samples that are compared for contamination.

19. A method for correcting pcd for the hydrocarbon staining of a reservoir rock sample to account for one or more end member components and background material that does not constitute indigenous hydrocarbon staining, the method comprising the steps of:

a. providing a sample of drilled reservoir rock removed from a known location;

b. obtaining pcd for the sample;

c. calculating the HC yield for the sample from the pcd;

d. subtracting interfering components that are contaminants for each data point comprising the pcd to provide a corrected pcd;

e. recalculating the pyrolytic parameters LV, TD, TC and $T_{min}$ based on the corrected pcd;

f. recalculating API gravity, POPI, $POPI_{norm}$ and Apparent Water Saturation based upon the recalculated parameters obtained in step (e); and g. recording for retention and analysis the results of the calculations of step (f).

20. The method of claim 19, wherein the corrected yield, $Yield_{corr}$, at a given data point X is calculated to remove the effects of interfering components $EM_1$ and $EM_2$ as follows:

$Yield_{corr}=Yield_{STEPX}-((\% EM_1/100)*Yield_{EM1,X}*(THC_{sample}/THC_{EM1}))+(\% EM_2/100)*Yield_{EM2,X}*(THC_{sample}/THC_{EM2}))$.

21. The method of claim 19 which includes the further steps of graphically displaying for analysis the pyrogram curves corresponding to (a) the pcd of the reservoir rock sample, (b) the pcd of the interfering components and (c) the corrected pcd.

22. A method for directly assessing moved hydrocarbons in a reservoir rock sample removed from a well drilled using drilling mud, said drilling mud formed from a plurality of additives, the method comprising the steps of:

a. providing a sample of drilled reservoir rock removed from a known location in the well bore;

b. obtaining pcd from one or more of the plurality of drilling mud additives for a predetermined quantity of the sample obtained in step (a);

c. comparing the pcd of the one or more of the plurality of additives produced in step (b) with pre-existing pcd of the one or more of the drilling mud additives; and d. recording for retention and comparative analysis the respective pcd values.

23. A method of optimizing the placement of horizontal power water injector wells in an oil field containing tar mats, the method comprising the steps of:

a. obtain a plurality of samples of reservoir rock from the oil field;

b. analyze each of the plurality of samples by pyrolysis;

c. perform compositional modeling based on one or more end members known to be present in the field;

d. correct the pyrolysis parameters for background or dispersed organic matter;

e. assess the values for $POPI_{Norm}$ and $AS_w$ in terms of relative position in the oil-water transition zone;

f. plot the results for the original and the corrected pyrolysis data;

g. plot the compositional modeling data;

h. determine whether the results of step (g) are consistent with the then-current well path directional drilling plan;

i. adjust the drilling program, as necessary, to optimize the well path location; and j. repeat steps (a) through (i).

24. A method for optimizing the placement of horizontal production wells through reservoir rock in an oil field, the method comprising the steps of:

a. obtain a plurality of the samples of reservoir rock from the oil field;

b. analyze each of the plurality of samples by pyrolysis;

c. perform compositional modeling, based on one or more end members known to be present in the field;

d. correct the pyrolysis parameters for background or dispersed organic matter;

e. assess the data to determine whether the pyrolytic characteristics for a sample from a known location are consistent with productive oil reservoir rock;

f. plot the results for the original and the corrected pyrolysis data;

g. plot the compositional modeling data;

h. determine whether the results of step (g) are consistent with the then-current well path directional drilling plan;

i. adjust the drilling program, as necessary, to optimize the well path location and continue to monitor; and j. repeat steps (a) through (i).

25. A method of identifying the relative proportions by percent of a plurality of hydrocarbon pollutant end-member components in one or more soil or aquifer samples taken from a selected geographical region by analysis of pyrolytic characterizing data (pcd), the method comprising the steps of:
 a. identifying the pollutant end-member components known or believed to be present in the soil or aquifer in the geographical region;
 b. preparing individual pyrograms consisting of pcd for each of the pollutant components identified in step (a);
 c. storing the pcd for each component in a digital data file;
 d. conducting a pyrolytic analysis of a sample from the geographical region that contains one or more hydrocarbon and organic matter components of the type identified in step (a) to obtain pcd for the sample;
 e. comparing the pcd for the sample with the pcd obtained in step (b) for each of the pollutant components, measuring and recording the difference between the sample pcd and the pcd for each of the components;
 f. applying a statistical analysis to minimize the aggregate differences between the pcd for the sample and a combination of pcd selected from the components;
 g. recording for retention and analysis the resulting pcd that constitutes the minimum aggregate error over the temperature range of the pyrolytic analysis; and
 h. identifying any one or more pollutant end members from the pcd.

26. The method of claim 25 which includes the further steps of providing one or more additional soil or aquifer samples from different locations, including different strata in the geographical region; and repeating steps (d) through (h) on each of the additional samples.

27. The method of claim 25 which includes the further steps of:
 i. providing one or more additional soil or aquifer samples from the same geographical region that are known or believed to be free of pollutants;
 j. identifying any indigenous non-pollutant end-member components that are found in the soil of aquifer samples of step (i);
 k. preparing invidual pyrograms consisting of the pcd for each of the any non-pollutant components found in step (j);
 l. comparing the pcd for the non-pollutant end-member components obtained in step (k) components;
 m. combining the pcd for the non-pollutant components with the pcd obtained in step (b); and
 n. repeating steps (e) through (h).

28. A method for identifying the presence of hydrocarbon pollutants in soil or aquifer samples from a specific geographic region, where the samples are subjected to pyrolytic analysis, the method comprising the steps of:
 a. providing a plurality of soil or aquifer samples removed from spaced-apart adjacent locations in the geographic region;
 b. subjecting the rock samples to pyrolytic analysis to obtain pcd consisting of a plurality of data points for each of the plurality of samples obtained in step (a);
 c. adjusting the pcd so that all samples have the same total yield of hydrocarbons;
 d. subtracting the pcd for a first sample having apparent pollution multiplied by the ratio of $$\frac{THC_{smp}X}{THC_{smp}X+1}$$

from the pcd of a second adjacent sample having greater apparent pollution at the plurality of data points;
 e. recording for retention and analysis a new adjusted pollution pcd based upon step (d); and
 f. identifying the nature and extent of the hydrocarbon pollutants in the geographical region from which the samples were removed.

\* \* \* \* \*